United States Patent [19]

Lauer et al.

[11] 4,026,936
[45] May 31, 1977

[54] ANTHELMINTIC PYRIDINE AND THIAZOLE SUBSTITUTED BENZIMIDAZOLE CARBAMATES

[75] Inventors: Rudolph Frank Lauer, Nutley; Armin Walser, West Caldwell, both of N.J.

[73] Assignee: Hoffmann-La Roche Inc., Nutley, N.J.

[22] Filed: Aug. 7, 1975

[21] Appl. No.: 602,695

[52] U.S. Cl. .................. 260/294.8 C; 260/295 F; 260/296 R; 260/297 R; 260/290 HL; 260/302 R; 260/302 H; 424/263; 424/270
[51] Int. Cl.[2] ........................................ C07D 235/32
[58] Field of Search ..... 260/309.2, 295 F, 294.8 R, 260/294.8 C

[56] References Cited

UNITED STATES PATENTS 3,657,267   4/1972   Van Gelder et al. ........... 260/309.2

OTHER PUBLICATIONS

Van Gelder et al., Chem. Abstracts, vol. 74(19), 100,047s, May 10, 1971.
Burger, Medicinal Chemistry, Second Edition, pp. 78–79, RS 403 B.8 1960 C.7.

*Primary Examiner*—Alan L. Rotman
*Attorney, Agent, or Firm*—Samuel L. Welt; Bernard S. Leon; Gerald S. Rosen

[57] ABSTRACT

Compounds represented by the formula

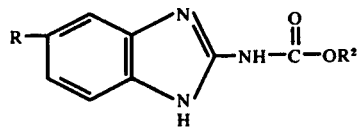

wherein
R is

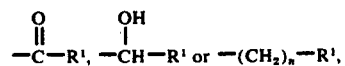

$R^1$ is 2-pyridyl, 3-pyridyl, 4-pyridyl or 2-thiazyl,
$R^2$ is lower alkyl and $n$ is 1 or 2, and acid addition salts of the compounds wherein $R^1$ is 2-pyridyl, 3-pyridyl or 4-pyridyl are disclosed as useful as anthelmintics against a broad spectrum of helminths. Processes for making the active compounds and novel intermediates useful therein are also disclosed.

13 Claims, No Drawings

ANTHELMINTIC PYRIDINE AND THIAZOLE SUBSTITUTED BENZIMIDAZOLE CARBAMATES

DESCRIPTION OF THE INVENTION

This invention relates to 2-benzimidazole carbamates substituted at the 5(6) position with pyridinoyl, thiazoyl, pyridylhydroxymethyl, thiazylhydroxymethyl, pyridylmethyl or pyridylethyl useful as anthelmintics, process for preparing the active compounds and novel intermediates therefore.

The novel active compounds of this invention are represented by the formula

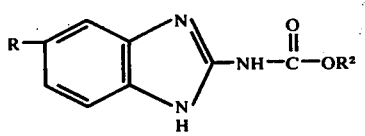

wherein
R is

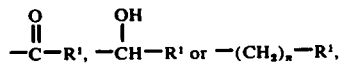

$R^1$ is 2-pyridyl, 3-pyridyl, 4-pyridyl or 2-thiazyl,
$R^2$ is lower alkyl and $n$ is 1 or 2,
and pharmaceutically acceptable acid addition salts of the compounds wherein $R^1$ is 2-pyridyl, 3-pyridyl or 4-pyridyl.

The compounds which are preferred are those in which $R^1$ is 2-pyridyl and $R^2$ is methyl or ethyl. Most preferred are those compounds in which R is

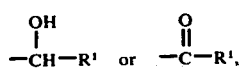

$R^2$ is methyl and
$R^1$ is 2-pyridyl.

As used herein, "lower alkyl" includes straight and branched chain alkyl radicals having from 1 to 7 carbon atoms, e.g., methyl, ethyl, propyl, isopropyl, butyl, t-butyl, hexyl, pentyl and the like. The term "pharmaceutically acceptable acid addition salts" includes salts of pharmaceutically acceptable strong acids with weak bases, e.g., hydrochloric acid, hydrobromic acid, sulfuric acid, acetic acid, succinic acid, maleic acid, benzene sulfonic acid, toluene sulfonic acid, methanesulfonic acid and the like.

The active acyl compounds are prepared by cyclizing an appropriately substituted 0-diamine with the appropriate N-carboxy-isothiourea.

The active hydroxy compounds are prepared by reduction of the acyl compounds.

The compounds of this invention are prepared by the following general reactions:

Step 1

$R^1$ is 2, 3 or 4 pyridyl.

The reaction is carried out at elevated temperatures, e.g., reflux temperature of thionyl chloride, and the resulting product is converted to the ketone by Friedel-Crafts acylation of chlorobenzene using aluminum chloride according to the following:

Step 2

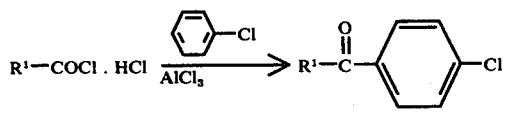

wherein $R^1$ is 2, 3 or 4-pyridyl.

The ketones can also be produced by oxidizing 2-(p-chlorobenzyl)pyridine with sodium dichromate in refluxing acetic acid according to the following:

Step 3

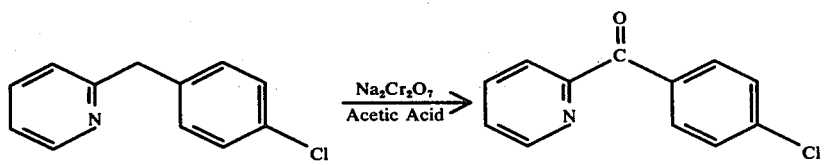

The alcohols wherein $R^1$ is 2-thiazyl, 2, 3 or 4-pyridyl are prepared by reacting the appropriate bromo compound, e.g., 2-bromopyridine, with n-butyl lithium at low temperatures, e.g., −78° C., to form the lithio salt which is then reacted with p-chlorobenzaldehyde at low temperatures, e.g., −78° C. to result in an alcohol. In order to obviate a subsequent nitration step, 3-nitro-4-chlorobenzaldehyde can be used instead of p-chlorobenzaldehyde. The reaction is illustrated as follows:

Step 4

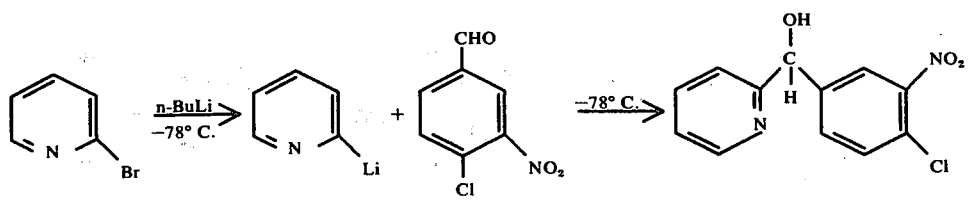

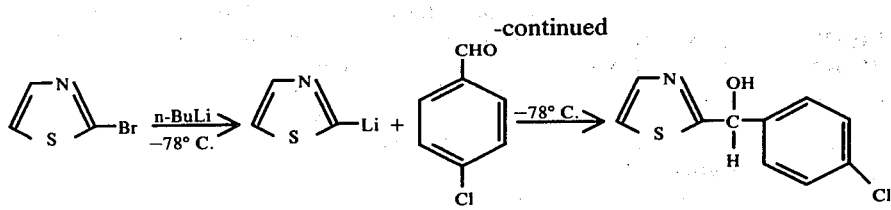

The resulting alcohols are oxidized with chromium trioxide in hot acetic acid to the ketones. The ketones from Steps 2 and 3 which do not have a nitro substituent are then nitrated with potassium nitrate in sulfuric acid. The following illustrates the reactions:

Step 5

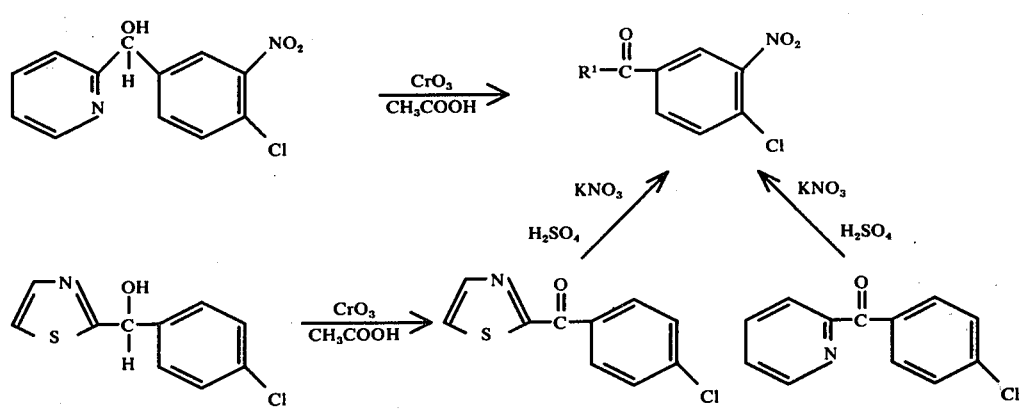

$R^1$ is 2-thiazyl, 2, 3 or 4-pyridyl.

The diamines are prepared by reacting the ketones from Step 5 with saturated ammonia in ethanol in an autoclave heated to about 100° C. followed by reduction of the nitro group with hydrogen in ethanol using a conventional hydrogenation catalyst, e.g., palladium on carbon, Raney nickel and the like. The resulting product need not be isolated but can be directly used to react with the appropriate N-carboxy-isothiourea to form the final products of this invention.

The following depicts the formation of the diamine:

Step 6

The diamine is converted to the 2-benzimidazole carbamate active compounds by reacting it with the appropriate N-carboxy-isothiourea at elevated temperatures, e.g., about 80° to 100° C., in acetic acid. The resulting product can be converted to the corresponding alcohol, which is also anthelmintically active, by reduction with sodium borohydride in tetrahydrofuran at room temperature. The following illustrates the reactions.

Step 7

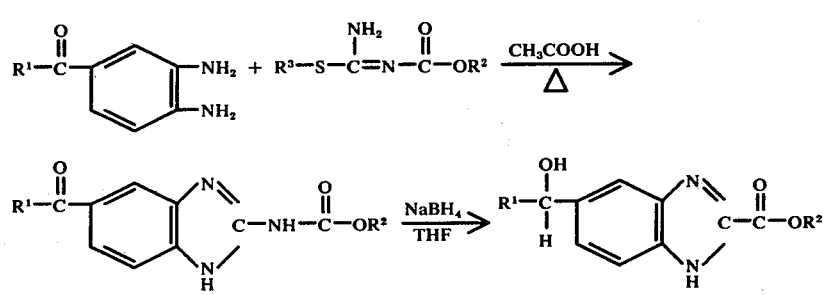

$R^1$ is 2-thiazyl, 2, 3 or 4-pyridyl,
$R^2$ is lower alkyl, and
$R^3$ is lower alkyl.

The pyridyl methyl and pyridyl ethyl compounds of this invention can be prepared by nitrating the appropriate p-chlorobenzyl or parachlorophenethyl pyridine with fuming nitric acid. The resulting nitro compound is then aminated with ammonia in ethanol in an auto-

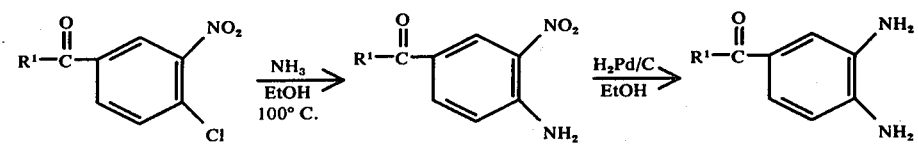

$R^1$ is 2-thiazyl, 2, 3 or 4-pyridyl.

clave at 180° C. The resulting nitro-amine is converted to the diamine by catalytic reduction with a conventional hydrogenation catalyst, e.g., palladium on carbon, Raney nickel and the like. The diamine is then converted to the 2-benzimidazole carbamate by reaction with the appropriate N-carboxy isothiourea at temperatures of about 80° to 100° C. in acetic acid. The following illustrates the reactions:

Step 8

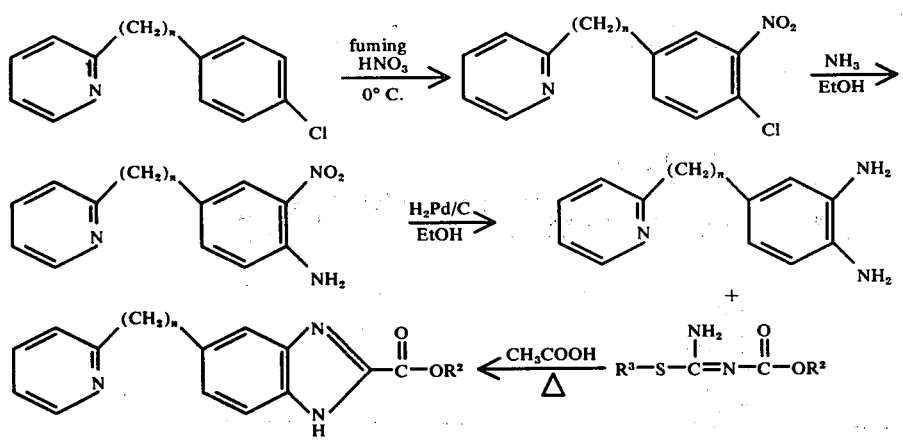

$R^2$ is lower alkyl,
$R^3$ is lower alkyl and n is 1 or 2.

In each of Steps, 4, 5 and 8 where a pyridyl substituent is depicted, it represents a 2, 3 or 4-pyridyl substituent.

The 2-benzimidazole carbamates of this invention have been found to possess valuable anthelmintic properties. The compounds are particularly useful against various helmintic infections of the intestinal tract of domestic as well as economically important animals such as cats, dogs, sheep, cattle, swine, chickens and the like. The compounds are active against a broad spectrum of helminths although every compound encompassed by this invention does not have an identical spectrum or intensity of activity. The compounds are active against Ascaris, Heterakis, Nematosphiroides, Syphacia Fasciola, Strongyloides, Ostertagia, Hymenolepis and the like. Depending on the weight of the host animal, dosages of about 1 to about 200 mg./kg. of body weight daily will generally be sufficient to effectively clear the animal of the infectious organisms. Anthelmintic compositions comprising an effective amount of an active compound either alone or in combination with other active therapeutic ingredients in admixture with suitable carriers may be readily prepared according to conventional pharmaceutical and veterinary techniques for the usual routes of administration.

The compounds are effective when administered in feed at levels of about 0.00625 to 0.1% by weight in drinking water at levels of about 0.022 to 0.35% by weight. Higher levels can, of course, be used, however, the criteria to be followed is that a sufficient amount be administered to provide a daily intake sufficient to provide protection against helminths. In addition to conventional parenteral, enteral or oral dosage forms the compound can be combined with, for example, feed and drinking water.

The most preferred compounds are methyl[5(6)-2-pyridinoyl-benzimidazol-2-yl]carbamate and methyl[5(6)-(2-pyridylhydroxymethyl)benzimidazol-2-yl]carbamate.

The preferred process of making the active compounds of this invention is the process which starts at Step 3.

The following tests in mice illustrate the anthelmintic activity of the compounds of this invention.

The test for activity against Hymenolepis nana is conducted on laboratory mice and the compounds are administered orally in feed. Four mice per group are used in the test. One group is the infected unmedicated control (IUC), another group is the uninfected unmedicated control (UUC). In testing for activity against Hymenolepis nana and Nematospiroides dubius the test compound is given two weeks after infection for a total of eight days after which the mice are sacrificed and the intestinal worms counted and compared to the IUC. The results are calculated as percent reduction in worms as compared to the IUC.

In testing for activity against Ascaris suum the test compound is started 24 hours before infection and continued for eight days after which the mice are sacrificed and the larvae in the lungs counted and compared to the IUC. The results are calculated as percent reduction in larvae as compared to the IUC.

In testing for activity against Syphacia obvelata the test compound is given for eight days to naturally infected mice after which the mice are sacrificed and the cecal worms counted and compared to the IUC. The results are calculated as percent reduction in worms as compared to the IUC.

A compound is considered active if the percent reduction in the described tests is 80–100%.

The following illustrates the results of tests utilizing the compounds of this invention. The results are compared to methyl[5(6)-benzoyl-2-benzimidazole]-carbamate (mebandazole), a known anthelmintic.

TABLE I

| Compound | % by Weight in Diet | Activity Based on % Reduction | | | |
|---|---|---|---|---|---|
| | | N. dubius | A. suum | S. obvelata | H. nana |
| Methyl[5(6)-3-pyridinoyl-2-benzimidazolyl]carbamate | 0.05 | − | + | + | − |
| Methyl[5(6)-(4-pyridinoyl)-2-benzimidazolyl]carbamate | 0.05 | − | + | + | − |

TABLE I-continued

| Compound | % by Weight in Diet | Activity Based on % Reduction | | | |
|---|---|---|---|---|---|
| | | N. dubius | A. suum | S. obvelata | H. nana |
| Ethyl[5(6)-4-pyridinoyl-2-benzimidazolyl]carbamate | 0.05 | − | + | + | − |
| Ethyl[5(6)-3-pyridinoyl-2-benzimidazolyl]carbamate | 0.05 | − | + | + | − |
| Methyl[5(6)-(2-thiazoyl)-2-benzimidazolyl]carbamate | 0.1 | − | ± | + | ± |
| Ethyl[5(6)-2-thiazoyl-2-benzimidazolyl]carbamate | 0.05 | − | ± | + | + |
| Methyl[5(6)-(2-pyridylhydroxymethyl)benzimidazol-2-yl]carbamate | 0.05 | + | + | + | + |

+ is greater than 90% reduction
± is from 50 to 90% reduction
− is less than 50% reduction

TABLE II

| Compound | % by Weight in Diet | Activity Based on % Reduction | | | |
|---|---|---|---|---|---|
| | | A. suum | N. dubius | S. obvelata | H. nana |
| Methyl[5(6)-2-pyridinoyl-2-benzimidazolyl]carbamate | 0.1 | + | + | + | + |
| | 0.05 | + | + | + | + |
| | 0.025 | NT | − | + | − |
| | 0.0125 | + | − | + | − |
| | 0.00625 | NT | − | + | − |
| Mebendazole | 0.05 | − | ± | + | − |
| | 0.025 | − | − | + | − |
| | 0.0125 | − | − | + | − |

+ is greater than 90% reduction
± is from 50 to 90% reduction
− is less than 50% reduction
NT is not tested.

In tests for activity against Trematodes and Nematodes in sheep, the sheep were treated with a single oral dose of the test compound for 10 days then sacrificed and the worms were recovered and counted. The results were compared to the IUC and expressed as percent reduction.

TABLE III

| Compound | Dosage ng/kg Body Weight | Trematodes (Fasciola hepatica) | % Reduction Strongyles (Ostertagia spp.) | Strongyloides (Strongyloides papillosus) |
|---|---|---|---|---|
| IUC | 0 | 0 | 0 | 0 |
| Methyl[5(6)-2-pyridinoyl-2-benzimidazolyl]carbamate | 50 | 86 | 100 | 100 |
| | 10 | 6 | 100 | 81 |
| Methyl[5(6)-(2-pyridylhydroxymethyl)benzimidazol-2-yl]-carbamate | 50 | 43 | 100 | 25 |
| | 10 | 0 | 100 | 0 |

Reductions over 80% are evidence of an active compound.

In tests for activity against gastrointestinal nematodiasis in lambs, the lambs were infected with *Hemonchus comtorus*, *Trichostrongylus colubriformis* or *nematodirus spathiger* 24 days before treatment. The lambs were treated with a single oral dose of test compound and 7 days after treatment the animals were sacrificed and the worms recovered and counted. The results were compared to IUC and expressed as percent reduction.

Example 1

Methyl[5(6)-2-pyridinoyl-2-benzimidazolyl]carbamate

A solution of 15.9 g. (0.0746 mol) of 2-(3,4-diaminobenzoyl)pyridine and 14.8 g. (0.1 mol) of N-(methoxycarbonyl)-S-methylisothiourea in 50 ml. of acetic acid was heated to 80°–90° C. for 4 hrs., cooled to room temperature and diluted with 25 ml. of water. The resulting product was collected, washed with 2-propanol, water and ether to yield the crude product as a gray-brown solid. Purification was accomplished by dissolving the solid in 200 ml. of hot 2N hydrochloric acid, treated with Norite, filtering and neutralizing the filtrate with 200 ml. of 25% ammonium hydroxide. The resulting solid was collected washed with water and

TABLE IV

| Compound | Dose mg/kg | % Reduction Compared to Control | | |
|---|---|---|---|---|
| | | Hemonchus contortus | Trichostrongylus colubriformis | Nematodirus spathiger |
| IUC | 0 | 0 | 0 | 0 |
| Methyl[5(6)-(2-pyridinoyl)2-benzimidazoyl]carbamate | 20 | 100 | 100 | 50 |
| | 20 | 99.3 | 69.2 | 3.1 |
| | 10 | 97.3 | 100 | 0 |
| | 10 | 97.3 | 76.9 | 53.6 |
| | 5 | 94.9 | 92.3 | 35.7 | dissolved in 5 l. of boiling 4:1 tetrahydrofuran-methanol. Filtration, concentration to 1500 ml. and dilution with 500 ml. of benzene caused crystallization of the product. Concentration of the filtrate gave a second crop. The product methyl[5(6)-2-pyridinoyl-2-benzimidazolyl]carbamate was recovered as light yellow microprisms, mp>300° C. (dec.).

Methyl[5(6)-2-pyridinoyl-2-benzimidazolyl]carbamate was also prepared when a 2-fold excess of N-(methoxycarbonyl)-S-ethylisothiourea was used as the cyclizing agent in place of N-(methoxycarbonyl)-S-methylisothiourea.

Example 2

Methyl[5(6)-(2-pyridylhydroxymethyl)benzimidazol-2-yl]carbamate

A mixture of 5.5 g. (0.0186 mol) of methyl[5(6)-(2-pyridinoyl)-2-benzimidazolyl]carbamate and 5.5 g. (0.15 mol) of sodium borohydride in 700 ml. of tetrahydrofuran was stirred for 48 hrs., diluted with 100 ml. of water, filtered and concentrated in vacuo. The resulting residue was suspended in water, filtered and recrystallized from ethyl acetate to yield methyl[5(6)-(2-pyridylhydroxymethyl)benzimidazol-2-yl]carbamate as white microprisms, mp >300° C. (dec.)

Example 3

Ethyl[5(6)-(2-pyridinoyl)-2-benzimidazolyl]carbamate

A solution of 6.2 g. (0.029 mol) of 2-(3,4-diaminobenzoyl)pyridine and 10.2 g. (0.058 mol) of N-(ethoxycarbonyl)-S-ethylisothiourea in 20 ml. of acetic acid was heated to 80°–90° C. overnight, cooled to room temperature and diluted with 20 ml. of 2-propanol. The resulting solid was collected, washed with 2-propanol and ether to yield ethyl[5(6)-(2-pyridinoyl)-2-benzimidazolyl]carbamate as an off-white crystalline solid, mp. >300° C. (dec.).

Example 4

Ethyl[5(6)-(4-pyridinoyl)-2-benzimidazolyl]carbamate

A solution of 7.8 g. (0.037 mol) of 4-(3,4-diaminobenzoyl)pyridine and 13 g. (0.074 mol) of N-(ethoxycarbonyl)-S-ethylisothiourea in 20 ml. of acetic acid was heated to 80°–90° C. overnight, cooled to room temperature and diluted with 20 ml. of 2-propanol. The resulting solid was recrystallized from tetrahydrofuran (Norite) to yield white microprisms, mp. >300° C. (dec.)

Ethyl[5(6)-(4-pyridinoyl)-2-benzimidazolyl]carbamate can also be prepared using N-(ethoxycarbonyl)-S-methylisothiourea as the cyclizing agent in place of N-(ethoxycarbonyl)-S-ethylisothiourea.

Example 5

Ethyl[5(6)-(3-pyridinoyl)-2-benzimidazolyl]carbamate

A solution of 8 g. (0.0375 moles) of 3-(3,4-diaminobenzoyl)pyridine and 12.2 g. (0.075 mol) of N-(ethoxycarbonyl)-S-methylisothiourea in 25 ml. of acetic acid was heated to 85° C. for two hours, cooled to room temperature and diluted with 20 ml. of 2-propanol. The resulting product was collected, washed with 2-propanol and ether to yield ethyl[5(6)-3-pyridinoyl-2 -benzimidazolyl]-carbamate as an off-white solid. Purification was accomplished by dissolving 5.0 g. of the product in 100 ml. of 2N hydrochloric acid at 65° C., treating with Norite, filtering and neutralizing with 100 ml. of 25% ammonium hydroxide. The resulting solid was collected, washed with water, dissolved in 400 ml. of DMF at 100° C. filtered and diluted with 400 ml. of water. Crystallization at room temperature yielded ethyl[5(6)-(3-pyridinoyl)-2-benzimidazolyl]-carbamate as white microprisms, mp. >300° C. (dec.) (tetrahydrofuran).

Example 6

Methyl[5(6)-(3-pyridinoyl)-2-benzimidazolyl]carbamate

A solution of 8 g. (0.0375 mol) of 3-(3,4-diaminobenzoyl)pyridine and 12.2 g. (0.075 mol) of N-(methoxycarbonyl)-S-ethylisothiourea in 25 ml. of acetic acid was heated to 85° C. for 2 hrs. The mixture was then cooled to room temperature and diluted with 25 ml. of 2-propanol. The resulting product was collected, washed with 2-propanol and ether to yield methyl[5(6)-(3-pyridinoyl)-2-benzimidazolyl]carbamate as an off-white solid. Purification was accomplished by dissolving 5.0 g. of the product in 100 ml. of 2N hydrochloric acid at 65° C., treating with Norite, filtering and neutralizing with 100 ml. of 25% ammonium hydroxide. The resulting solid was collected, washed with water, dissolved in 400 ml. of DMF at 100° C., filtered and diluted with 400 ml. of water. Crystallization at room temperature yielded methyl[5(6)-(3-pyridinoyl)-2-benzimidazolyl]carbamate as white microprisms, mp. >300° C. (dec.) (tetrahydrofuran-methanol).

Example 7

Ethyl[5(6)-(2-thiazoyl)-2-benzimidazolyl]carbamate

A solution of 7.5 g. (0.034 mol) of 2-(3,4-diaminobenzoyl)thiazole and 11.4 g. (0.07 mol) of N-(ethoxycarbonyl)-S-methylisothiourea in 25 ml. of acetic acid was heated to 85° C. for 4 hrs. The resulting solution was cooled to room temperature and diluted with 25 ml. of water. The resulting product was collected, washed with 2-propanol and ether to yield ethyl[5(6)-(2-thiazoyl)-2-benzimidazolyl]carbamate as a greenish white solid. The product was then dissolved in 200 ml. of DMF at 100° C., treated with Norite, filtered and diluted with 100 ml. of water. The resulting product crystallized overnight at room temperature to yield ethyl[5(6)-(2-thiazoyl)-2-benzimidazolyl]carbamate as light yellow microprisms, mp. >300° C. (dec.) (tetrahydrofuran).

Example 8

Methyl[5(6)-(2-thiazoyl)-2-benzimidazolyl]carbamate

The same procedure as for the preparation of ethyl[5(6)-(2-thiazoyl)-2-benzimidazolyl]carbamate was used except a 2-fold excess of the cyclizing agent N-(methoxycarbonyl)-S-methylisothiourea was used in place of N-(ethoxycarbonyl)-S-methylisothiourea to yield methyl[5(6)-(2-thiazoyl)-2-benzimidazolyl]carbamate as light yellow microprisms, mp. >300° C. (dec.) tetrahydrofuran.

Example 9

Methyl[5(6)-(4-pyridinoyl)-2-benzimidazolyl]carbamate

A solution of 7.5 g. (0.034 mol) of 4-(3,4-diaminobenzoyl)pyridine and 11.4 g. (0.07 mol) of N-(methoxycarbonyl)-S-methylisothiourea in 25 ml. of acetic acid was heated to 85° C. for 4 hrs. The resulting solution was cooled to room temperature and diluted with 25 ml. of water. The resulting product was collected, washed with 2-propanol and ether. The crude product was then dissolved in 200 ml. of DMF at 100° C., treated with Norite, filtered and diluted with 100 ml. of water. The resulting product crystallized overnight at room temperature to yield methyl[5(6)-(4-pyridinoyl)-2-benzimidazolyl]carbamate as light yellow prisms, mp. >300° C. (pyridine).

Example 10

2-(3-nitro-4-aminobenzoyl)pyridine

A suspension of 63 g. (0.24 mol) of 2-(3-nitro-4-chlorobenzoyl)pyridine in 3 liters of a saturated solution of ammonia in ethanol was autoclaved at 100° C. for 24 hrs. The mixture was concentrated in vacuo and the resulting residue dissolved in 1.5 liters of warm 5N hydrochloric acid. The solution was cooled to room temperature and neutralized with concentrated ammonium hydroxide. The resulting yellow product was collected, washed with water and dried to yield 2-(3-nitro-4-aminobenzoyl)pyridine, mp. 186°–187° C. (acetone-water).

Example 11

2-(4-chlorobenzoyl)pyridine 15 g. of picolinic acid and 80 g. of thionyl chloride were heated together for 90 min. on a water bath, excess thionyl chloride was distilled off in vacuum, the residue was treated with 80 ml. of chlorobenzene and 58 grams of aluminum trichloride. The resulting mixture was stirred at room temperature overnight and worked up with water and sodium hydroxide to yield 2-(4-chlorobenzoyl)-pyridine as white microprisms, mp. 62°–64° C. (ligroin).

Example 12

2-(3-Nitro-4-chlorobenzoyl)pyridine 15.5 g. (0.153 mol) of potassium nitrate was added portionwise to a stirred solution of 33 g. (0.152 mol) of 2-(4-chlorobenzoyl)pyridine in 200 ml. of sulfuric acid, while maintaining the temperature below 40° C. After 1 hour the mixture was cautiously poured into 2 liters of ice water and neutralized with ammonium hydroxide. The resulting product 2-(3-nitro-4-chlorobenzoyl)pyridine was collected as white microneedles, mp. 98°–99° C. (cyclohexane).

Example 13

3-(4-chlorobenzoyl)pyridine 15 g. of nicotinic acid and 80 g. of thionyl chloride were heated together for 90 minutes on a water bath. Excess thionyl chloride was distilled off in a vacuum. The residue was treated with 80 ml. of chlorobenzene and 58 g. of aluminum trichloride. The mixture was stirred overnight and worked up as in Example 11 to yield white microprisms of 3-(4-chlorobenzoyl)pyridine, mp. 90°–91° C.

Example 14

4-(4-chlorobenzoyl)pyridine 15 g. of isonicotinic acid and 80 g. of thionyl chloride were heated together for 90 minutes on a water bath. Excess thionyl chloride was distilled off in a vacuum. The residue was treated with 80 ml. of chlorobenzene and 58 g. of aluminum trichloride. The resulting mixture was stirred at room temperature overnight to yield white microprisms of 4-(4-chlorobenzoyl)pyridine, mp. 112°–113° C.

Example 15

3-(3-Nitro-4-chlorobenzoyl)pyridine 15.5 g. (0.153 mol) of potassium nitrate was added portion-wise to a stirred solution of 33 g. (0.152 mol) of 3-(4-chlorobenzoyl)pyridine in 200 ml. of sulfuric acid while maintaining the temperature below 40°. After 1 hr. the mixture was cautiously poured into 2 liters of ice-water, neutralized with ammonium hydroxide and the product collected to yield 3-(3-nitro-4-chlorobenzoyl)pyridine as yellow prisms, mp. 112°–113° C. (carbon tetrachloride-Norite).

Example 16

4-(3-Nitro-4-chlorobenzoyl)pyridine 15.5 g. (0.153 mol) of potassium nitrate was added portion-wise to a stirred solution of 33 grams (0.152 mol) of 4-(4-chlorobenzoyl)pyridine in 200 ml. of sulfuric acid while maintaining the temperature below 40° C. After one hour the mixture was cautiously poured into 2 liters of ice-water, neutralized with ammonium hydroxide and the product collected to yield 4-(3-nitro-4-chlorobenzoyl)pyridine as yellow prisms, mp. 114°–116° C. (cyclohexane-Norite).

Example 17

N-(Methoxycarbonyl)-S-methylisothiourea 5 ml. of water and 1.9 ml. of dimethyl sulfate were added to 1.52 g. of thiourea (20 mmol). The mixture was stirred for about 3 mins. (until the initial heat evolution had subsided). The clear solution was then heated on a steam bath for 1 hour with stirring. The solution was cooled to about 20° C. and surrounded by a water bath (18°–22° C.). Freshly distilled methyl chloroformate (3.1ml., 40 mmol) was added all at once followed by dropwise addition of 25 ml. of 10% aqueous sodium hydroxide over a period of 30 mins. The resulting product was isolated by extraction with methylene chloride and concentrated in vacuo to give an oily yellow solid which crystallized from ether as white prisms, mp. 97°–100° C.

Example 18

N-(Ethoxycarbonyl)-S-methylisothiourea

The procedure of Example 17 was followed using ethyl chloroformate instead of methyl chloroformate. The product was isolated by extraction with ether and concentration in vacuo to a yellow oil which solidified slowly on standing.

Example 19

N-(Ethoxycarbonyl)-S-ethylthiourea 302 g. (2.78 moles) of ethyl chloroformate was added to 2 moles of S-ethylisothiourea hydrochloride in 800 ml. of water and 200 ml. of acetonitrile. A 25% solution of sodium hydroxide was added dropwise so rapidly that, with external cooling, a temperature of +25° C. was not exceeded. The solution of sodium hydroxide was added for as long as the pH value did not rise above 8. Stirring was effected for a further 80 minutes during which control of the pH value was continued. If necessary, a little more solution of sodium hydroxide was added. A two phase system, aqueous and organic, resulted. The product was isolated from the organic phase by extraction with methylene chloride and concentration in vacuo to a light yellow oil.

Example 20

N-(Methoxycarbonyl)-S-ethylisothiourea

The procedure of Example 19 was followed except methyl chloroformate was used in place of ethyl chloroformate. The product was isolated by extraction with ether and concentration in vacuo to a light yellow oil.

Example 21

3-Nitro-4-chlorophenyl-2-pyridyl methanol

A solution of 200 ml. (0.32 mol) of n-butyllithium in 400 ml. of tetrahydrofuran was added to a solution of 48 g. (0.286 mol) of 2-bromopyridine in 120 ml. of tetrahydrofuran under argon cooled to −78° C. over 20 min. After 30 min. the resulting dark orange mixture was transferred under argon into a solution of 50 g. (0.27 mol) of 4-chloro-3-nitrobenzaldehyde in 600 ml. of tetrahydrofuran over a 30 min. period and the resulting dark solution was allowed to warm to room temperature overnight. The mixture was hydrolyzed with 32 g. (0.1 mol) of sodium sulfate decahydrate, filtered and concentrated in vacuo to a dark oil which was then warmed to 80° C. in 300 ml. of 3N hydrochloric acid, then cooled to 10° C. and the product was filtered, washed successively with 2-propanol and ether to yield 3-nitro-4-chlorophenyl-2-pyridylmethanol as its hydrochloride, mp. 195°–205° C.

The free base was obtained as yellow microprisms, mp. 120°–120.5° C. (methylene chloride-ether).

Example 22

2-(3-Nitro-4-chlorobenzoyl)pyridine

A solution of 27 g. (0.27 mol) of chromium trioxide in 250 ml. of water was added to a solution of 80 g. (0.266 mol) of 3-nitro-4-chlorophenyl-2-pyridyl methanol hydrochloride in 800 ml. of 75% acetic acid at 45° C. and the mixture was heated to 75° C. for 1 hr. The resulting dark green solution was poured into 3 liters of ice-water. The resulting product was filtered off, washed with water, dissolved in methylene chloride, dried with sodium sulfate and concentrated in vacuo to yield 2-(3-nitro-4-chlorobenzoyl)pyridine as white microneedles, mp. 98°–99° C. (cyclohexane).

Example 23

2-(3,4-Diaminobenzoyl)pyridine

A suspension of 20 g. (0.082 mol) of 2-(3-nitro-4-aminobenzoyl)pyridine in 1 liter of tetrahydrofuran containing 5 g. of 5% palladium on carbon was reduced with hydrogen under a pressure of 3 atmospheres. The resulting mixture was filtered and concentrated in vacuo to a reddish oil which was dissolved in a minimum amount of methylene chloride and diluted with petroleum ether to yield 2-(3,4-diaminobenzoyl)pyridine as a slightly unstable yellow solid, mp. 137Z°–138° C. (water).

Example 24

3-(3-Nitro-4-aminobenzoyl)pyridine

A suspension of 63 g. (0.24 mol) of 3-(3-nitro-4-chlorobenzoyl)pyridine in 3 liters of a saturated solution of ammonia in ethanol was autoclaved at 100° C. for 24 hours. The mixture was concentrated in vacuo and the resulting residue dissolved in 1.5 liters of warm 5N HCl. The solution was cooled to room temperature and neutralized with concentrated ammonium hydroxide. The resulting product was collected as yellow-orange prisms, mp. 229°–230° C. (dimethylformamide-2-propanol).

Example 25

4-(3-Nitro-4-aminobenzoyl)pyridine

The procedure of Example 24 was followed except 4-(3-nitro-4-chlorobenzoyl)pyridine was used in place of 3-(3-nitro-4-chlorobenzoyl)pyridine. The product was orange prisms, mp. 294°–295° C. (dimethylformamide-2-propanol).

Example 26

4-(3,4-Diaminobenzoyl)pyridine

A suspension of 20 g. (0.082 mol) of 4-(3-nitro-4-aminobenzoyl)pyridine in 1 liter of tetrahydrofuran containing 5 g. of 5% palladium on carbon was reduced with hydrogen under a pressure of 3 atmospheres. The resulting mixture was filtered and concentrated in vacuo to reddish oil which was dissolved in a minimum amount of methylene chloride and diluted with petroleum ether to yield 4-(3,4-diaminobenzoyl)pyridine as an unstable orange solid, mp. 210°–214° C. (water-Norite).

Example 27

4-Chlorophenyl-2-thiazylmethanol

A solution of 67.5 g. (0.41 mol) of 2-bromothiazole in 180 ml. of tetrahydrofuran was added over a 20 min. period to a solution of 225 ml. (0.45 mol) of n-butyllithium (in hexane) in 600 ml. of tetrahydrofuran at −78° C. under argon. After 30 min. this solution was transferred under argon to a solution of 52.8 g. (0.375 mol) of p-chlorobenzaldehyde in 900 ml. of tetrahydrofuran at −78° C. The reaction was then allowed to warm to room temperature overnight. Sodium sulfate decahydrate (32 g., 0.1 mol) was added, the mixture filtered and concentrated in vacuo to yield the crude product as a red-brown oil which slowly solidified. An analytical sample was evaporatively distilled at 180° C./1 mm Hg. to yield a light yellow oil, which solidified rapidly, and the solid recrystallized from ether-pentane, mp. 74.5°–75° C.

Example 28

2-(4-Chlorobenzoyl)thiazole

A solution of 51 g. (0.51 mol) of chromium trioxide in 300 ml. of 66% acetic acid was added to a solution of 130.5 g. of crude 4-chlorophenyl-2-thiazylmethanol in 1200 ml. of acetic acid at 60° and the mixture stirred for 1.5 hr. at 80° C. The resulting solution was poured into 4 liters of ice-water. The resulting product was collected and recrystallized from acetone-water to yield 2-(4-chlorobenzoyl)thiazole as white prisms, mp. 101°–103° C.

Example 29

2-(3-Nitro-4-chlorobenzoyl)thiazole

Potassium nitrate (2.1 g., 0.02 mol) was added in one portion to a solution of 4.5 g. (0.02 mol) of 2-(4-chlorobenzoyl)thiazole in 25 mol. of concentrated sulfuric acid. After 1 hr. the mixture was cautiously poured into 250 ml. of ice water, the product collected, washed with water and dried to yield 2-(3-nitro-4-chlorobenzoyl)thiazole as pale-yellow prisms, mp. 118°–119° (acetone-water).

Example 30

2-(3-Nitro-4-aminobenzoyl)thiazole

A suspension of 63. g. (0.24 mol) of 2-(3-nitro-4-chlorobenzoyl)thiazole in 3 liters of a saturated solution of ammonia in ethanol was autoclaved at 100° C. for 24 hrs. The mixture was concentrated in vacuo and the resulting residue dissolved in 1.5 liters of warm 5N hydrochloric acid. The solution was cooled to room temperature and neutralized with concentrated ammonium hydroxide to yield 2-(3-nitro-4-aminobenzoyl)-thiazole as yellow-orange prisms, mp. 179°–181° C. (methanol).

Example 31

2-(3,4-diaminobenzoyl)thiazole

A suspension of 20 g. (0.082 mol) of 2-(3-nitro-4-aminobenzoyl)thiazole in 1 liter of tetrahydrofuran containing 5g. of 5% palladium on carbon was reduced with hydrogen under a pressure of 3 atmospheres. The resulting mixture was filtered and concentrated in vacuo to yield 2-(3,4-diaminobenzoyl) thiazole as unstable red needles, mp. 125°–127° C. (dec.) (acetone-water).

Example 32

2-(4-Chlorobenzoyl)pyridine

164 G (0.55 mol) of sodium dichromate was added to a stirred solution of 101 g. (0.5 mol) of 2-(p-chlorobenzyl)-pyridine in 450 mol. of acetic acid and the resulting mixture was stirred and refluxed for 3 hrs. The resulting dark green solution was cooled and poured into 1500 ml. of cold water. The precipitate which resulted was collected, washed with water and air dried to yield 2-(4-chlorobenzoyl)pyridine as white microprisms, mp. 62–64° C. (ligroin).

Example 33

Methyl[5(6)-(4-pyridylhydroxymethyl)benzimidazol-2-yl] carbamate

7 G. (184 mmol) of sodium borohydride was added to a stirred suspension of 7 g. (23.6 mmol)of methyl [5(6)-4-pyridinoyl-2-benzimidazoyl] carbamate in 1.5 l. of tetrahydrofuran. After 24 hours, 70 ml. of water and 70 ml. of acetic acid were added and the resulting solution was concentrated in vacuo. The solid which resulted was suspended in water, filtered. air-dried then dissolved in 2 l. of 4:1 ethyl acetate-methanol and filtered again. Upon concentration of the resulting solution to 500 ml. methyl[5(6)-(4-pyridylhydroxymethyl)-benzimidazol-2-yl]carbamate crystallized as white microprisms, mp. 250° C. (dec.) (ethyl acetate).

Example 34

2-(4-Chloro-3-nitrobenzyl)pyridine

99 G. (0.487 mol) of 2-(p-chlorobenzyl)pyridine was added to 500 ml. of fuming nitric acid cooled to 10 ° while maintaining the temperature at <10° for 2 hours. The resulting mixture was poured into 800 ml. of ice, neutralized with ammonium hydroxide and allowed to stand overnight at room temperature. The resulting solid was collected, washed with water and air dried to give 2-(4-chloro-3-nitrobenzyl)pyridine as off-white prisms, m. 58°–60° C. (aq. ethanol).

Example 35

2-(4-Amino- 3-nitrobenzyl)pyridine

Ethanol(1700 ml.) was saturated with ammonia at −20° to a total volume of 3l., then 49.7 g. (0.2 mol) of 2-(4-chloro-3-nitrobenzyl)pyridine was added. The entire mixture was first autoclaved at 100° C. for 24 hours, then 185° C. for 24 hours. The resulting solution was then evaporated in vacuo to a brown solid, which was thereafter dissolved in acetone, dried with magnesium sulfate. filtered and evaporated in vacuo to a light brown solid. The resulting solid was crystallized from water using Norite to give 2-(4-amino-3-nitrobenzyl)-pyridine as yellow-orange prisms, mp. 128°–132° C. (water).

Example 36

Methyl[5(6)-(2-pyridinylmethyl)-2-benzimidazolyl]-carbamate 1 g. of 5% palladium on carbon was added to a suspension of 9.8 g. (42.7 mmol) of 2-(4-amino-3-nitrobenzyl)pyridine in 280 ml. of absolute ethanol. The resulting mixture was reduced with hydrogen in a Paar shaker. After 7 hours reaction time the resulting mixture was filtered through Celite and evaporated in vacuo to a brown solid which was dissolved in 25 ml. of acetic acid. 11.8 g. (80 mmol) of N-(methoxycarbonyl)-S-methylisothiourea was added to the brown solid. After heating the resulting mixture to 100° for 3 hours, it was cooled to room temperature. 25 ml. of water was then added and then enough ammonium hydroxide was dropped in to give a pH ≈8. The resulting product was collected, washed with water, 2-propanol and ether to yield methyl[5(6)-2-pyridinylmethyl)-2-benzimidazolyl carbamate as a light tan powder, mp. 234°–236° C. (methanol).

We claim:

1. A compound represented by the formula

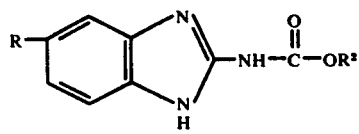

wherein R is

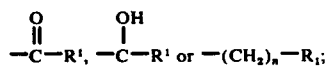

$R^1$ is 2-pyridyl, 3-pyridyl, or 4-pyridyl and $R^2$ is lower alkyl and $n$ is 1 or 2, and pharmaceutically acceptable acid addition salts of the compounds wherein $R^1$ is 2-pyridyl, 3-pyridyl or 4-pyridyl.

2. A compound of claim 1 wherein R is

3. A compound of claim 2 wherein $R^1$ is 2-pyridyl and $R^2$ is methyl.

4. A compound of claim 1 wherein $R^1$ is 2-pyridyl and $R^2$ is ethyl.

5. A compound of claim 1 wherein $R^1$ is 3-pyridyl and $R^2$ is methyl.

6. A compound of claim 1 wherein $R^1$ is 3-pyridyl and $R^2$ is ethyl.

7. A compound of claim 1 wherein $R^1$ is 4-pyridyl and $R^2$ is methyl.

8. A compound of claim 1 wherein $R^1$ is 4-pyridyl and $R^2$ is ethyl.

9. A compound of claim 1 wherein R is

10. A compound of claim 9 wherein $R^1$ is 2-pyridyl and $R^2$ is methyl.

11. A compound of claim 1 wherein R is $-(CH_2-)_n-R^1$.

12. A compound of claim 1 wherein R is $-CH_2-R^1$.

13. A compound of claim 12 wherein $R^1$ is 2-pyridyl and $R^2$ is methyl.

* * * * *